(12) United States Patent
Kyomoto et al.

(10) Patent No.: US 9,216,241 B2
(45) Date of Patent: *Dec. 22, 2015

(54) MEDICAL DEVICE AND METHOD FOR PRODUCING THE SAME

(75) Inventors: Masayuki Kyomoto, Osaka (JP);
Kazuhiko Ishihara, Tokyo (JP); Kozo Nakamura, Tokyo (JP); Yoshio Takatori, Tokyo (JP); Hiroshi Kawaguchi, Tokyo (JP); Toru Moro, Tokyo (JP)

(73) Assignees: KYOCERA MEDICAL CORPORATION, Osaka (JP); THE UNIVERSITY OF TOKYO, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/809,690

(22) PCT Filed: Dec. 19, 2008

(86) PCT No.: PCT/JP2008/073218
§ 371 (c)(1),
(2), (4) Date: Oct. 20, 2010

(87) PCT Pub. No.: WO2009/081870
PCT Pub. Date: Jul. 2, 2009

(65) Prior Publication Data
US 2011/0027757 A1 Feb. 3, 2011

(30) Foreign Application Priority Data
Dec. 21, 2007 (JP) ................................ 2007-330917

(51) Int. Cl.
A61L 33/00 (2006.01)
A61L 27/34 (2006.01)
A61L 31/10 (2006.01)
A61K 6/04 (2006.01)
A61K 6/033 (2006.01)

(52) U.S. Cl.
CPC ............. *A61L 33/0076* (2013.01); *A61K 6/033* (2013.01); *A61K 6/04* (2013.01); *A61L 27/34* (2013.01); *A61L 31/10* (2013.01); *Y10T 428/31667* (2015.04)

(58) Field of Classification Search
CPC ....... A61K 6/0023; A61K 6/033; A61K 6/04; C08L 33/08; C08L 33/10; A61L 27/34; A61L 31/10; A61L 33/0076; Y10T 428/31667
See application file for complete search history.

(56) References Cited

U.S. PATENT DOCUMENTS 5,453,467 A 9/1995 Bamford et al.
2003/0190405 A1* 10/2003 Bowers et al. ............... 427/2.1
2007/0260112 A1 11/2007 Rahmani
2008/0292778 A1* 11/2008 Tarcha et al. .............. 427/2.25
2009/0317443 A1* 12/2009 Willis et al. .................. 424/423
2010/0168512 A1 7/2010 Rahmani
2010/0262237 A1 10/2010 Kyomoto et al.

FOREIGN PATENT DOCUMENTS

JP 06-510322 11/1994
JP 2000-212376 8/2000
JP 2009-536083 10/2009
WO 2007/116690 10/2007

OTHER PUBLICATIONS

Goda et al ("Biomimetic phosphorylcholine polymer grafting from polydimethylsiloxane surface using photo-induced polymerization," Biomaterials 27 (2006) 5151-5160).*
English translation of the International Preliminary Report on Patentability and Written Opinion dated Jul. 20, 2010.
International Search Report issued Feb. 24, 2009 in International (PCT) Application No. PCT/JP2008/073218.
Extended European Search Report issued Nov. 29, 2012 in corresponding European Application No. 08865567.5.
Wang, Yikang, et al., "Covalent coupling of an phospholipid monolayer on the surface of ceramic materials", Chem. Commun., No. 7, 2000, pp. 587-588.
Japanese Office Action issued Sep. 10, 2013 in corresponding Japanese Application No. 2009-547801.
Wei Feng et al.; "Adsorption of Fibrinogen and Lysozyme on Silicon Grafted with Poly (2-methacryloyloxyethyl Phosphorylcholine) via Surface-Initiated Atom Transfer Radical Polymerization"; Langmuir; 2005; vol. 21, No. 13; pp. 5980-5987.
Shin'ichiro Kihara et al.; "In Vivo Evaluation of a MPC Polymer Coated Continuous Flow Left Ventricular Assist System"; Artificial Organs; vol. 27, No. 2; 2003; pp. 188-192.
Masayuki Kyomoto et al.; "High lubricious surface of cobalt-chromium-molybdenum alloy prepared by grafting poly (2-methacryloyloxyethyl phosphorylcholine)"; Biomaterials; vol. 28; 2007; pp. 3121-3130.

* cited by examiner

*Primary Examiner* — Suzanne Ziska
(74) *Attorney, Agent, or Firm* — Wenderoth, Lind & Ponack, L.L.P.

(57) ABSTRACT

An object is to provide a medical device having excellent antithrombotic and sliding characteristics, which can exert a cell adhesion inhibitory effect. A medical device comprising: a substrate capable of forming hydroxyl groups; and a biocompatible material layer laminated on the substrate at an appropriate position, wherein the hydroxyl groups are formed on a surface of the substrate at least at a required position by a surface treatment, while the biocompatible material layer is formed from a polymer containing phosphorylcholine groups, and wherein the substrate and the biocompatible material layer are joined via a binder layer formed from silica being covalently bonded with the hydroxyl groups and the biocompatible material, respectively.

9 Claims, 8 Drawing Sheets

MEDICAL DEVICE AND METHOD FOR PRODUCING THE SAME

This application is a U.S. national stage of International Application No. PCT/W2008/073218 filed Dec. 19, 2008.

TECHNICAL FIELD

The present invention relates to a medical device, and more particularly to a medical device which may come into contact with blood and biotissues, such as a blood pump for an (auxiliary) artificial heart, an artificial valve, a stent or a pacemaker, and a dental implant.

BACKGROUND ART

Metallic materials used for medical devices (for example, an (auxiliary) artificial heart, an artificial valve, a stent, a pacemaker, etc.) almost satisfy the conditions with respect to mechanical properties, but have not necessarily sufficient biocompatibility (including blood compatibility). When blood components come into contact with a surface of a medical device to form thrombus because of insufficient biocompatibility of the medical device, inhibition of blood flow arises, resulting in serious harm to the human body. Therefore, in clinical practice, a drug capable of inhibiting a biological defense reaction is required in a therapeutic action using a medical device and the side effect caused by use of this drug over a long period constitutes a large problem. A biocompatible (including blood compatibility) material is indispensable to develop a medical device which can be used in the state of being embedded in the living body over a long period.

In current medical practice, a method using a biologically active substance capable of inhibiting thrombus formation is used so as to impart antithrombotic properties to a surface of a medical device, for example, an artificial organ. This method includes, for example, a method of immobilizing a biologically active substance such as urokinase having a function of dissolving thrombus thus formed, heparin capable of inhibiting a function of thrombin as a coagulation factor, or prostaglandin as a platelet activation inhibitor to a surface of a material. However, the side effect caused by these drugs cannot be neglected and is a large problem. It is very difficult to control the release rate of the drug and also the effect cannot be expected after release of the drug. Furthermore, a non-biocompatible polymer, for example poly(lactide-co-ε-caprolactone), poly(n-butyl methacrylate) or poly(dimethylsiloxane) is often used in a drug eluting type medical device (particularly stent) and, after elution of the drug, a polymer remaining on a stent surface may cause inflammatory reaction and thrombus formation. Furthermore, there is reported a problem that endothelialization does not occur on the stent surface.

In order to impart antithrombotic properties to a surface of a medical device, for example, an artificial organ, a method utilizing a biological reaction is employed. That is, it is a method in which coagulation factors and platelets are moderately aggregated to a surface of a material to form a thrombus membrane, and endothelial cells constituting a vascular wall are engrafted on the thrombogenic membrane as a footing and a thin neointima is formed on the surface of the material by further growth of the endothelial cells. However, since thrombus may occur for about one month after surgery during which the medical device has been completely coated with endothelial cells, it becomes necessary to administer an antiplatelet drug and thus the side effect caused by the drug cannot be neglected.

There is also employed a method in which antithrombotic properties are obtained by surface properties of the material per se without using a biologically active substance or a drug. By the way, thrombus formation occurs due to an adsorption of a plasma protein and a subsequent activation of platelets, and the adsorption of the plasma protein onto the surface of the material physicochemically proceeds. Therefore, in order to decrease the interaction between the material and blood, the surface of the material is converted into the state almost as close to blood as possible by reforming the surface of the material.

Such a reforming method includes, for example, a method in which a water-soluble polymer is bonded by a coupling reaction utilizing functional groups such as hydroxyl and amino groups of the surface of the material.

For example, a method for immobilizing a copolymer consisting of allylamine and a monomer having a phosphorylcholine group to a medical material is disclosed (Patent Document 1). However, when the copolymer is used, there arises a problem that the content of the phosphorylcholine group decreases and the resulting material is inferior in biocompatibility (including blood compatibility), hydrophilicity and surface lubricity. In contrast, when the content of the phosphorylcholine group in the copolymer is excessive, there arises a problem that the copolymer becomes soluble in water and adhesion is not maintained when used for a long time. Actually, an artificial heart made of metallic titanium coated with an MPC copolymer contains only 30% of MPC in the MPC copolymer because of a problem of solubility (Non-Patent Document 1).

Another reforming method includes a method in which peroxide as a polymerization initiator is produced on a surface of a material by irradiating with ultraviolet rays, electric beams or ion beams in the presence of oxygen, and then a water-soluble vinyl monomer is subjected to radical polymerization to form a water-soluble polymer chain on the surface of the material. It is reported that this water-soluble polymer chain prevents a protein from being directly contacted with the surface of the material and inhibits the adsorption of the protein onto the surface of the material.

For example, Kazuhiko Ishihara et al. succeeded in an improvement of anti-protein adsorption property by MPC-grafting as a monomer on a polyethylene surface through irradiation with ultraviolet rays. However, this is a technology concerning a polymer substrate and it is impossible to easily reform a surface of a metal substrate. There is also disclosed a report that a poly(MPC) layer formation on a cobalt-chromium alloy is carried out with use of 4-methacryloxyethyl trimellitate anhydride (4-META) as a binder, and as a result, excellent hydrophilicity and lubricating properties are obtained (Non-Patent Document 2). However, there is also reported a problem that the cobalt-chromium alloy cannot be completely coated.

Taking a dental implant into account, there has conventionally been carried out a prosthetic treatment with retrievable partial denture or bridge denture for repairing a loss of teeth due to periodontal diseases and dental caries. However, retrievable partial denture has an aesthetic problem attributed from a metal hook and a problem of providing a feeling of resistance to implementation, while bridge denture has a problem that burden for abutment tooth to be grinded cannot be avoided. A dental implant treatment has attracted special interest recently as a prosthetic treatment and is one of selection choices, and the number of cases has remarkably increased. In loss of teeth due to fracture of an alveolar bone, teeth are lost together with the alveolar bone around teeth and thus bone width and bone height enough to carry out embedding of implant were not often obtained. However, it has become possible to apply a bone grafting method, a guided bone regeneration (GBR) method, a bone lengthening method, a bone prosthetic material, and a bone augmentation method utilizing cytokines, thus increasing the number of cases of application of a dental implant. In some cases, it becomes possible to impart an occlusion function through embedding due to one-stage implant and mounting of an upper structure at an initial stage after embedding, by improving surface properties of an implant or controlling a load on an implant body after embedding. Establishment of a method of early and surely acquiring osseointegration remarkably contributes to stabilization of the occlusion function of the dental implant. However, even if osseointegration is acquired, it is impossible to persistently avoid the circumstance in which the implant body as foreign matters penetrates through the epithelium. Therefore, how plaque deposition in this gingival penetration portion is inhibited and inflammation around the implant body is prevented, was an important object for enabling the dental implant to function over a long period. Particularly in two-stage implant, the micro-gap existing between the abutment and the fixture bonding portion makes it easy to cause inflammation around the implant. Also, local bone resorption temporarily occurs due to a removal of the bond formed on so-called healing cap or the top portion of the implant body during secondary surgery, and thus down growth of gingival epithelia is likely to occur, thus leading to the state where plaque deposition is likely to occur, and esthetics may sometimes deteriorate, which is a clinical problem.

Patent Document 1: International Publication No. WO 01-05855

Non-Patent Document 1: In Vivo Evaluation of a MPC Polymer Coated Continuous Flow Left Ventricular Assist System, ARTIFICIAL ORGANS, VOL. 27, No. 2, 2003

Non-Patent Document 2: High lubricious surface of cobalt-chromium-molybdenum alloy prepared by grafting poly(2-methacryloyloxyethyl phosphorylcholine), Biomaterials, VOL. 28, 2007

DISCLOSURE OF THE INVENTION

Problems to be Solved by the Invention

In light of these problems, the present invention has been made and an object thereof is to provide a medical device having excellent antithrombotic and sliding characteristics which is less likely to cause thrombus even when used in vivo over a long period and is therefore capable of excluding use of a drug inhibiting a biological defense reaction, and a method for producing the same; and a dental implant which can exert a cell adhesion inhibitory effect and also can inhibit dental plaque deposition and periodontal diseases.

Means for Solving the Problems

A medical device according to the present invention is a medical device comprising: a substrate capable of forming hydroxyl groups; and a biocompatible material layer laminated on the substrate at an appropriate position, wherein the hydroxyl groups are formed on a surface of the substrate at least at a required position by a surface treatment, while the biocompatible material layer is formed from a polymer containing phosphorylcholine groups, and wherein the substrate and the biocompatible material layer are joined via a binder layer formed from silica being covalently bonded with the hydroxyl group and the biocompatible material, respectively.

A method for producing a medical device according to the present invention comprises, in the, production of a medical device including a biocompatible material layer laminated thereon at an appropriate position, a) a step of surface-treating a substrate formed from a material containing a metal component capable of forming hydroxyl groups to form the hydroxyl groups on a surface of the substrate, b) a step of forming a binder layer formed from silica containing a photopolymerization initiator on the substrate using the hydroxyl groups as a starting point, and c) a step of immersing the substrate in a solution containing a biocompatible material and irradiating with ultraviolet rays, thereby polymerizing the biocompatible material at an appropriate position to form a biocompatible material layer on the binder layer.

In the present invention, the medical device means a device used in vivo, and components thereof, and examples of the device used in vivo include an (auxiliary) artificial heart, an artificial valve, a stent, a pacemaker and a dental implant. In the case of the (auxiliary) artificial heart, examples of the component of the device include a pump casing, an impeller, a shaft constituting the impeller, a rotor and a fin, and an inlet port and an outlet port communicating with the pump casing. In the case of the dental implant, examples of the component include a fixture, an abutment and an abutment screw.

Effects of the Invention

According to the present invention, a surface of a medical device is coated with a material having biocompatibility and is less likely to cause thrombus even if the medical device is used in vivo over a long period, and therefore it is not necessary to use a drug capable of inhibiting a biological defense reaction, which may causes the side effect. Since a substrate of a medical device is bonded with a biocompatible material via a silica layer, firm adhesion can be realized. Also, since so-called graft-from polymerization, which enables direct growth of a biocompatible material layer from an acryloyl group or a methacryloyl group in the silica layer, is used upon production, the concentration of the biocompatible material in the biocompatible material layer can be increased, thus making it possible to obtain a medical device having more excellent antithrombotic properties and slidability. When the medical device of the present invention is used as a dental implant, a cell adhesion inhibitory effect can be obtained by the biocompatible material layer, thus making it possible to inhibit dental plaque deposition and periodontal diseases.

Therefore, according to the present invention, it is possible to provide a medical device having more excellent antithrombotic properties and slidability, which is less likely to cause thrombus even when used in vivo over a long period and therefore can eliminate a drug inhibiting a biological defense reaction, and a dental implant which can exert a cell adhesion inhibitory effect and can inhibit dental plaque deposition and periodontal diseases.

DESCRIPTION OF REFERENCE NUMERALS

Figure 1:
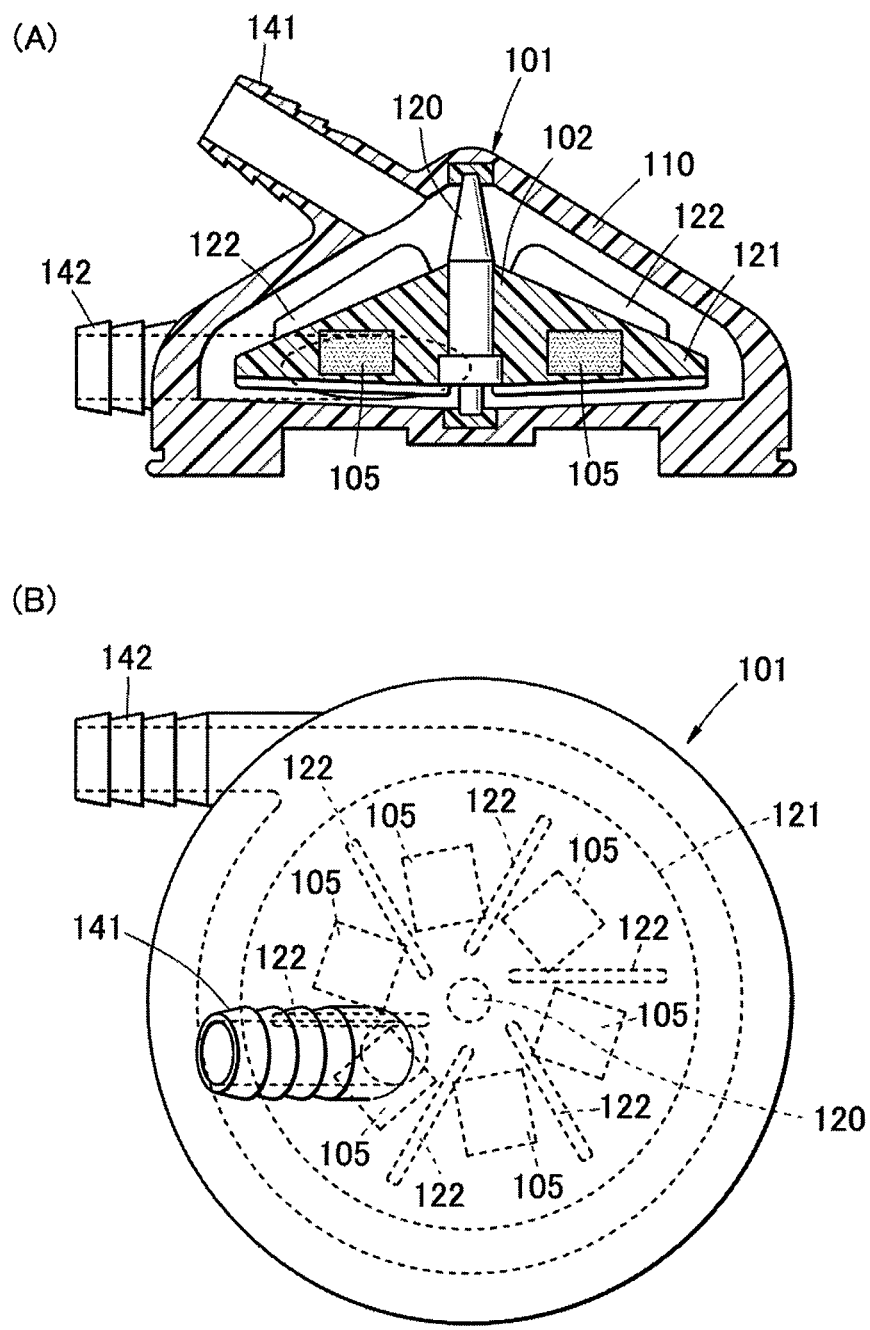
FIG. 1(A) is a schematic sectional view showing a cardiac blood pump according to the first embodiment of the present invention.
FIG. 1(B) is a plan view showing a cardiac blood pump.

1: Substrate
2: Surface-treated layer
3: Binder layer
4: Biocompatible material layer
101: Cardiac blood pump
102: Impeller
105: Magnet
110: Pump casing
120: Shaft
121: Rotor
122: Fin
141: Inlet port
142: Outlet port
201: Artificial dental root
202: Fixture
230: Abutment
240: Abutment screw

BEST MODE FOR CARRYING OUT THE INVENTION

A medical device according to embodiments of the present invention will be described in detail below with reference to the accompanying drawings. The following embodiments merely illustrate the present invention and the present invention is not limited to the embodiments.
(First Embodiment)

FIG. 1(A) is a schematic sectional view showing a cardiac blood pump 101 according to the first embodiment of the present invention, and FIG. 1(B) is a plan view showing the cardiac blood pump 101. The cardiac blood pump 101 is used as a blood delivery pump in an artificial heart-lung apparatus. As shown in FIG. 1(A), the cardiac blood pump 101 according to the present first embodiment is provided with a pump casing 110, and an impeller 102 rotatably supported in the pump casing 110. The impeller 102 includes a conical rotor 121 and a shaft 120 thereof, and plural fins 122 facing towards the casing inner surface are disposed on a conical surface of this rotor 121 in a centrifugal direction. In the vicinity of the top portion of the casing 110, an inlet port 141 of blood communicating with the top portion of the rotor 121, and an outlet port 142 of blood communicating with the bottom portion of the rotor 121 is disposed at an outer periphery side of a bottom portion 103 of the pump casing 110. A magnet 105 is embedded in the rotor 121 and the rotor 121 is rotatably driven by a rotating magnetic field generated by rotation of a magnet (not shown) outside the pump (for example, lowed side of the pump). These pump casing 110, the impeller 102 (the shaft 120, the rotor 121, and the fin 122), the inlet port 141 or the outlet port 142 constitute the substrate 1 according to the present invention.

Figure 2:
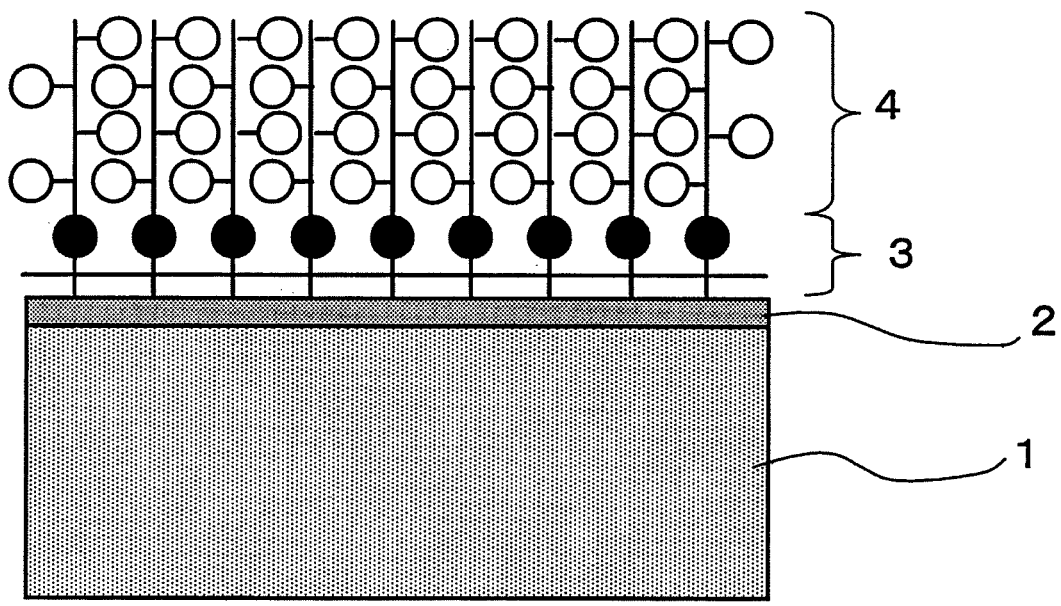
FIG. 2 is a schematic sectional view showing a cross section in the vicinity of a surface of a substrate.

FIG. 2 is a schematic sectional view showing a cross section in the vicinity of a surface of the cardiac blood pump 101 and components thereof. A substrate 1 corresponds to a base portion of the inlet port 141 or the outlet port 142 which communicates with the cardiac blood pump 101, the pump casing 110 and the impeller 102 which constitutes the cardiac blood pump 101, and the shaft 120 constituting the impeller 102, the rotor 121, the fin 122, and the pump casing. As shown in FIG. 2, a surface-treated layer 2 is formed on the substrate 1 as a result of a treatment of a surface and a binder layer 3 made of silica is laminated on the surface-treated layer 2, and also a biocompatible material layer 4 is laminated on the binder layer 3.

The surface-treated layer 2 is formed by treating the surface of the substrate 1 with an acid such as nitric acid. Hydroxyl groups are formed on the surface of the substrate 1 by treating the surface of the substrate 1 as described above, and this hydroxyl groups serve as a starting point of a dehydration condensation reaction of a silane coupling agent.

The silane coupling agent is hydrolyzed to form a silanol group, and the silanol group is bonded with the hydroxyl group formed on the surface of the surface-treated layer 2 through the dehydration condensation reaction. Furthermore, the silanol group is continuously bonded to form the binder layer 3 made of silica.

On the surface of the binder layer 3, for example, methacryloyl groups exist and serve as a starting point of the growth of a biocompatible material such as MPC. The methacryloyl group on the surface of the binder layer 3 is bonded with a functional group (for example, methacryloyl group) of the biocompatible material and also the biocompatible material continuously grows to form a biocompatible material layer 4 on the binder layer 3.

The binder layer 3 made of silica is firmly adhered to the substrate 1 and the biocompatible material layer 4, respectively, through a covalent bond. Therefore, it is possible to provide a medical device which can sufficiently endure a severe sliding operation and has high reliability of mechanical stability.

As the material of the substrate 1, for example, high-strength materials such as metal, alloy and ceramics can be used. A durable medical device with reliability can be provided by using these materials.

A sliding surface of the substrate 1 made of metal, alloy or ceramics is coated with the biocompatible material layer 4. Therefore, the generation of abrasive wear debris, which may exert an adverse influence of biotoxicity on the human body, of the substrate 1 is inhibited. Since the biocompatible material layer 4 is made of a polymer material such as MPC which does not exert an adverse influence on the living body, even if the abrasive wear debris is generated from the biocompatible material layer 4 during the sliding operation, the abrasive wear debris does not exert an adverse influence on the human body.
(Binder Layer)

As described above, the binder layer 3 is, for example, composed of silane alkoxide and is capable of firmly bonding the substrate 1 with the biocompatible material layer 4. It is possible to use, as the silane alkoxide, those exerting no influence on the human body, i.e. any kind of silane alkoxide can be used as long as it has biocompatibility.

The silane alkoxide used as the material of the binder layer 3 is represented by $R^1_x Si(OR^2)_{4-x}$ (X=0 to 3). $OR^2$ at one side is a hydrolyzed group and a silanol group (—SiOH) is formed by a hydrolysis reaction. Examples of $OR^2$ include $CH_3O$—, $C_3H_5O$— and $CH_3OC_2H_4O$—. OH in this silanol group is a hydrophilic polar group and silanol groups are bonded together by the dehydration condensation reaction. $R^1$ at the other side is an organic functional group and $R^1$ is preferably an acryloyl group or a methacryloyl group. These organic functional groups are preferable because they have polymerizability. The silanol group (—SiOH) is crosslinked by the dehydration condensation reaction to form a crosslinked structure such as a siloxane network (—Si—O—Si—), and thus the binder layer 3 made of silica is formed.

Herein, specific examples of the silane alkoxide used as the material of the binder layer 3 include methacryloyloxypropyltrimethoxysilane, methacryloyloxypropylmethyldimethoxysilane, methacryloyloxypropyltriethoxysilane and acryloyloxypropyltrimethoxysilane. Taking account of radical copolymerizability, the polymerizable group is preferably an acryloyl group or a methacryloyl group.

(Biocompatible Material Layer)

The biocompatible material is a material which has the same chemical structure as that of cells constituting biotissues and therefore exerts no adverse influence on the human because tissues in the living body does not cause rejection reaction even if the abrasive wear debris of the biocompatible material exists in the human body.

The biocompatible material according to the present invention is formed from a compound which is very close to that of the tissues of the inherent living cells, protein adsorption and formation of thrombus do not occur.

It is possible to use, as the biocompatible material, a polymer material having a phosphorylcholine group. The polymer material is preferably 2-methacryloyloxyethylphosphorylcholine, 2-acryloyloxyethylphosphorylcholine, 4-methacryloyloxybutylphosphorylcholine, 6-methacryloyloxyhexylphosphorylcholine, ω-methacryloyloxyethylenephosphorylcholine or 4-styryloxybutylphosphorylcholine. In view of polymerizability and ease of availability, MPC is particularly preferable.

Examples of the other biocompatible material include 3-methacryloyloxypropyl-2'-(trimethylammonio)ethylphosphate, 5-methacryloyloxypentyl-2'-(trimethylammonio)ethylphosphate, 2-methacryloyloxyethyl-2'-(triethylammonio) ethylphosphate, 2-methacryloyloxyethyl-2'-(tripropylammonio)ethylphosphate, 2-methacryloyloxyethyl-2'-(tributylammonio)ethylphosphate, 2-methacryloyloxybutyl-2'-(trimethylammonio)ethylphosphate, 2-methacryloyloxypentyl-2'-(trimethylammonio)ethylphosphate, 2-methacryloyloxyhexyl-2'-(trimethylammonio)ethylphosphate, 2-methacryloyloxyethyl-3'-(trimethylammonio)propylphosphate, 3-methacryloyloxypropyl-3'-(trimethylammonio)propylphosphate, 4-methacryloyloxybutyl-3'-(trimethylammonio)propylphosphate, 5-methacryloyloxypentyl-3'-(trimethylammonio)propylphosphate, 6-methacryloyloxyhexyl-3'-(trimethylammonio)propylphosphate, 2-methacryloyloxyethyl-4'-(trimethylammonio)butylphosphate, 3-methacryloyloxypropyl-4'-(trimethylammonio)butylphosphate, 4-methacryloyloxybutyl-4'-(trimethylammonio)butylphosphate, 5-methacryloyloxypentyl-4'-(trimethylammonio)butylphosphate and 6-methacryloyloxyhexyl-4'-(trimethylammonio)butylphosphate.

It is preferred that the biocompatible material layer is formed by covalent bonding of the polymer containing a phosphorylcholine group as a graft polymer chain. The biocompatible material layer having a predetermined thickness can be formed by grafting in such a manner. Herein, a radical may be generated on the substrate by irradiation with energy lines such as electric beams, gamma-rays and ultraviolet rays, or heating so as to graft the polymer. In particular, a new function can be efficiently imparted by using ultraviolet rays and a photopolymerization initiator without impairing properties of the substrate.

The thickness of the biocompatible material layer is preferably from 10 to 500 nm, and particularly preferably from 100 to 200 nm. When the thickness is adjusted within the above range, protein adsorption and formation of thrombus do not occur and also injury of tissues to be contacted with the substrate can be inhibited.

Regarding wettability of the biocompatible material layer with water, a contact angle is preferably not more than 30°. It is possible to increase lubricity of the medical device and to inhibit injury of tissues to be contacted with the medical device by adjusting the contact angle to not more than 30°.

The concentration of a phosphorus atom on a surface of the biocompatible material layer is preferably not less than 4 atomic %. Furthermore, both the concentration of a phosphorus atom and that of a nitrogen atom on the surface of the biocompatible material layer are preferably not less than 4.6 atomic %. Furthermore, in the case of using a surface grafted with an MPC polymer in combination with a surface grafted with an MPC polymer, a frictional coefficient can be remarkably decreased. Herein, it is preferred that the phosphorus atom on the surface of the biocompatible material layer is measured by X-ray photoelectron spectrometry.

(Substrate)

It is essential to use, as metal constituting the substrate 1, metal capable of forming a hydroxyl group on a surface of the metal by a surface treatment. Accordingly, the hydroxyl group on the surface is bonded by a covalent bond, thus enabling more firm adhesion. Examples of the metal include titanium (Ti) and chromium (Cr) which easily form a hydroxyl group, and examples of the alloy constituting the substrate 1 include stainless steel, a Cr alloy and a Ti alloy. Specific examples of preferable Cr alloy include a nickel-chromium alloy (Ni—Cr alloy), a cobalt-chromium alloy (Co—Cr alloy) and a cobalt-chromium-molybdenum alloy (Co—Cr—Mo alloy). These alloys are suitably used because they have biocompatibility. Specific examples of preferable Ti alloy include a Ti-6Al-4V alloy, a Ti-15Mo-5Zr-3Al alloy, a Ti-6Al-7Nb alloy, a Ti-6Al-2Nb-1Ta alloy, a Ti-15Zr-4Nb-4Ta alloy, a Ti-15Mo-5Zr-3Al alloy, a Ti-13Nb-13Zr alloy, a Ti-12Mo-6Zr-2Fe alloy, a Ti-15Mo alloy and a Ti-6Al-2Nb-1Ta-0.8Mo alloy. Similarly, these alloys are suitably used because they are excellent in biocompatibility. Furthermore, ceramics can be used as the material constituting the substrate 1. Examples of the ceramics include metal oxides capable of forming a hydroxyl group, such as alumina, zirconia and titania. In these materials, a hydroxyl group is easily formed on a surface by a plasma treatment and the hydroxyl group and a silanol group of a binder layer are firmly connected by covalent bonding. However, the material constituting the substrate 1 may be any material as long as it can form a functional group which can be covalently bonded with a silanol group of the binder layer 3 to be formed on the substrate 1. The functional group, which can be covalently bonded with a silanol group of the binder layer 3 to be formed on the substrate 1, is preferably a hydroxyl group but is not limited to the hydroxyl group.

An oxide layer is naturally formed on a surface only by subjecting alloys such as a Ni—Cr alloy, a Co—Cr alloy, stainless steel and Ti alloy to an alumina sandblasting treatment, and thus a higher adhesive strength is obtained. Since silane alkoxide exhibits high adhesion property to chromium hydroxide being formed from chromium oxide contained in alloys such as a Ni—Cr alloy and a Co—Cr alloy, a chromium-containing alloy is suitably used.

(Production Method)

The method for producing a cardiac blood pump according to the present first embodiment will be schematically described below.

First, a substrate 1 formed as a cardiac blood pump shown in FIG. 1 is prepared. Then, the substrate 1 is subjected to ultrasonic cleaning using a solvent. It is possible to use, as the solvent, acetone, methanol and ethanol.

When a Ni—Cr alloy, a Co—Cr alloy and stainless steel are selected as the material constituting the substrate 1, the concentration of chromium on the substrate surface can be increased by treating the surface of the substrate 1 with nitric acid. Accordingly, the concentration of Cr—OH to be formed on the substrate surface in the subsequent step can be increased and adhesion between the substrate 1 and the binder layer 3 can be improved.

Then, the substrate 1 treated with nitric acid is placed in a plasma treatment machine and subjected to an oxygen plasma treatment for 2 to 10 minutes to form a layer (Cr—OH) of high-density hydroxide on the surface of the substrate 1. The surface of the substrate 1 is converted into a surface-treated layer 2 by treating in such a manner.

Subsequently, silane alkoxide is dissolved in an organic solvent containing a photopolymerization initiator added therein, and then the substrate 1 is dipped in the solution. It is possible to use, as the organic solvent, methanol or ethanol. Herein, those described above can be used as the silane alkoxide. The concentration of the silane alkoxide is preferably within a range from 0.1% by weight to 10% by weight, and more preferably from 2% by weight to 5% by weight. When the concentration is within the above range, adhesion between the substrate 1 and the biocompatible material layer 4 can be satisfactorily carried out. The photopolymerization initiator to be used is preferably IRGACURE (D2959), IRGACURE (D369) or benzophenone, and most preferably IRGACURE (D2959).

Subsequently, the substrate coated as described above is dried under a normal pressure. Herein, the drying temperature is preferably from 40° C. to 120° C., and more preferably from 70° C. to 120° C. The drying time is from 0.5 hour to 3 hours, and more preferably from 1 hour to 3 hours.

Furthermore, the substrate is dipped in a solution prepared by dissolving a biocompatible material monomer in a solvent. Herein, it is possible to use, as the biocompatible material monomer, 2-methacryloyloxyethylphosphorylcholine, 2-acryloyloxyethylphosphorylcholine, 4-methacryloyloxybutylphosphorylcholine, 6-methacryloyloxyhexylphosphorylcholine, ω-methacryloyloxyethylenephosphorylcholine, 4-styryloxybutylphosphorylcholine, 3-methacryloyloxypropyl-2'-(trimethylammonio)ethylphosphate, 5-methacryloyloxypentyl-2'-(trimethylammonio)ethylphosphate, 2-methacryloyloxyethyl-2'-(triethylammonio)ethylphosphate, 2-methacryloyloxyethyl-2'-(tripropylammonio)ethylphosphate, 2-methacryloyloxyethyl-2'-(tributylammonio)ethylphosphate, 2-methacryloyloxybutyl-2'-(trimethylammonio)ethylphosphate, 2-methacryloyloxypentyl-2'-(trimethylammonio)ethylphosphate, 2-methacryloyloxyhexyl-2'-(trimethylammonio)ethylphosphate, 2-methacryloyloxyethyl-3'-(trimethylammonio)propylphosphate, 3-methacryloyloxypropyl-3'-(trimethylammonio)propylphosphate, 4-methacryloyloxybutyl-3'-(trimethylammonio)propylphosphate, 5-methacryloyloxypentyl-3'-(trimethylammonio)propylphosphate, 6-methacryloyloxyhexyl-3'-(trimethylammonio)propylphosphate, 2-methacryloyloxyethyl-4'-(trimethylammonio)butylphosphate, 3-methacryloyloxypropyl-4'-(trimethylammonio)butylphosphate, 4-methacryloyloxybutyl-4'-(trimethylammonio)butylphosphate, 5-methacryloyloxypentyl-4'-(trimethylammonio)butylphosphate and 6-methacryloyloxyhexyl-4'-(trimethylammonio)butylphosphate. Preferably, MPC can be used. The solvent is preferably water. Water may contain ethanol.

Subsequently, the substrate 1 is photo-irradiated with light thereby polymerizing the biocompatible material in the vicinity of the surface to form a biocompatible material layer 4. Proper wavelength of light is from 300 nm to 400 nm. Polymerization of the biocompatible material can be satisfactorily carried out using light having a wavelength within the above range. The concentration of a monomer of the biocompatible material is preferably from 0.25 to 1.00 mol/L, and more preferably from 0.50 to 1.00 mol/L. The polymerization temperature is preferably from 20° C. to 80° C., and more preferably about 60° C. The photo-irradiation time is preferably from 20 minutes to 180 minutes, and more preferably from 45 minutes to 90 minutes. The photo-irradiation radical polymerization reaction can be satisfactorily carried out by setting described above.

After completion of the photo-irradiation radical polymerization reaction, the substrate 1 is cleansed by dipping in water or an organic solvent. It is possible to use, as the organic solvent, methanol, ethanol or isopropyl alcohol, and ethanol is most preferable.

The cardiac blood pump according to the present first embodiment can be produced by the processes described above.

Figure 3:
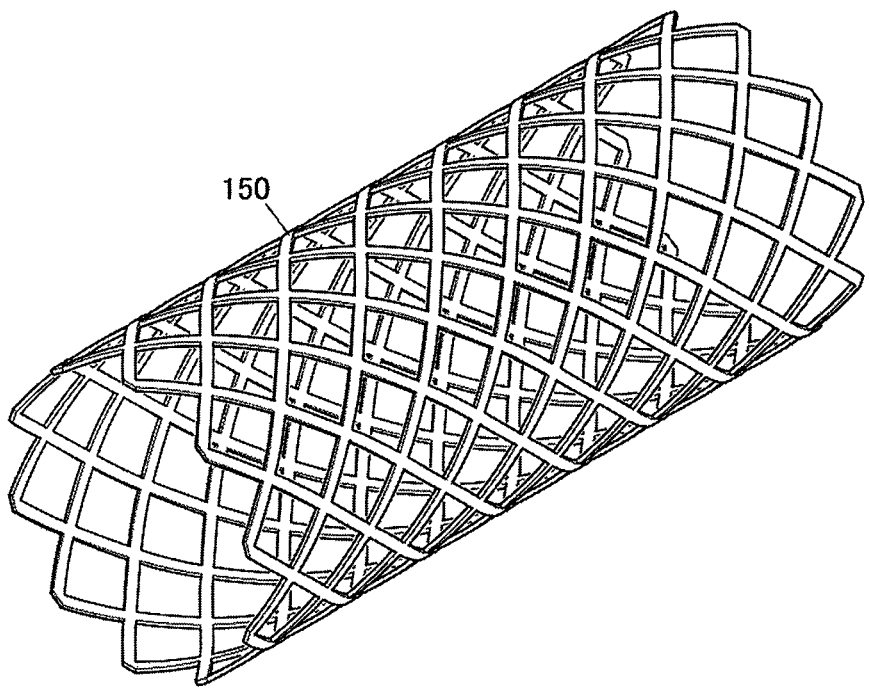
FIG. 3 is a perspective view showing a stent according to the present invention.
Figure 4:
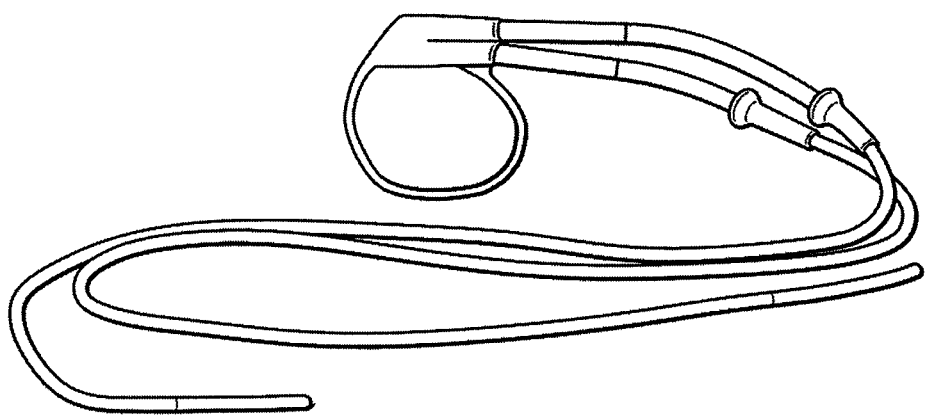
FIG. 4 is a perspective view showing a pacemaker according to the present invention.
Figure 5:
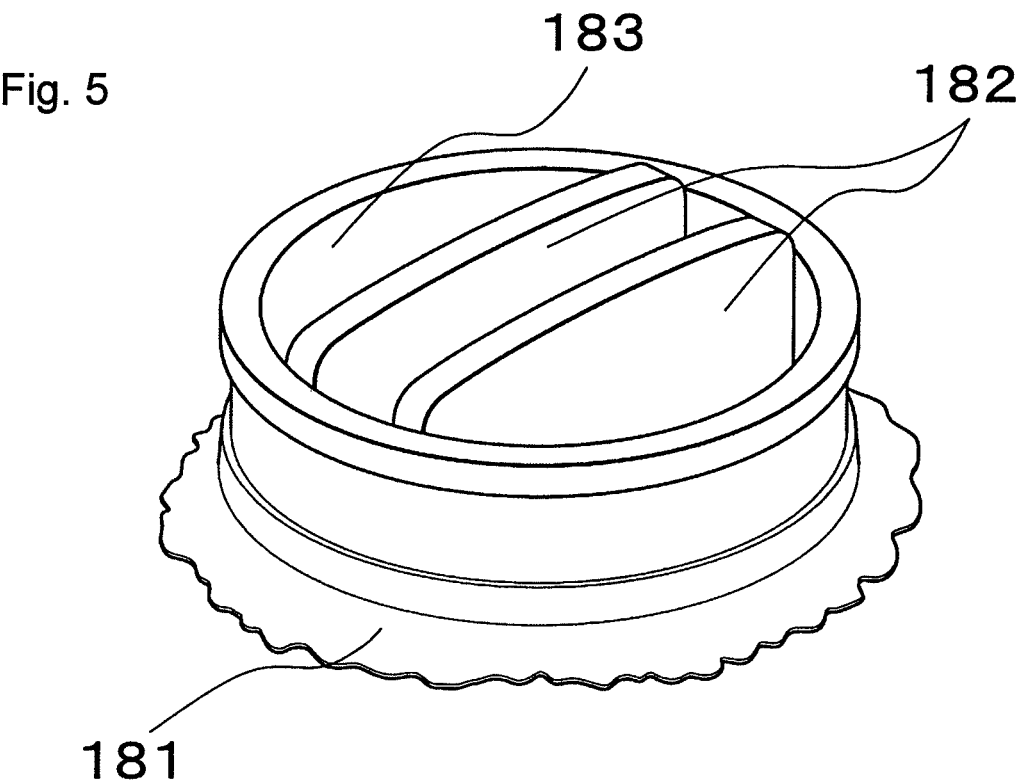
FIG. 5 is a perspective view showing an artificial valve according to the present invention.

Coating with the biocompatible material can also be applied to the stent, the pacemaker and the artificial valve shown in FIGS. 3 to 5.

FIG. 3 is a perspective view showing a stent according to the present invention. The stent is a medical device for expanding a tubular portion (blood vessel, trachea, esophagus, etc.) of the living body from the inside. As shown in FIG. 3, the stent can be composed of a network cylindrical body 150 made of metal. However, when the stent is, for example, used in a blood vessel, since blood is direct contact with the stent surface, thrombus may be formed. However, in the present invention, since inner and outer surfaces of the network cylindrical body 150 are coated with the biocompatible material layer as described above, thrombus formation is inhibited.

FIG. 4 is a perspective view showing a pacemaker according to the present invention. The pacemaker is, for example, an apparatus for causing cardiac contraction by generating electrical stimulation to cardiac muscle. The pacemaker includes an implantable pacemaker for permanent use and an extracorporeal pacemaker for temporary use. In the case of the implantable pacemaker, since it is contacted with blood or body fluid, a problem such as thrombus formation occurs. In the present invention, since the pacemaker is coated with the biocompatible material layer as described above, thrombus formation is inhibited.

FIG. 5 is a perspective view showing an artificial valve according to the present invention. When a cardiac valve is damaged, the artificial valve repairs the damaged portion and has a function of preventing back flow of blood. In the artificial valve, since an inner surface 183 and an opening/closing portion 182 thereof are always contacted with blood, thrombus may be formed. However, in the present invention, similar to the above, since the valve inner surface 183 and the opening/closing portion 182 are coated with the biocompatible material layer, thrombus formation is inhibited.

(Second Embodiment)

Subsequently, a dental implant according to the second embodiment of the present invention will be described in detail below with reference to FIGS. 6 to 8.

Figure 6:
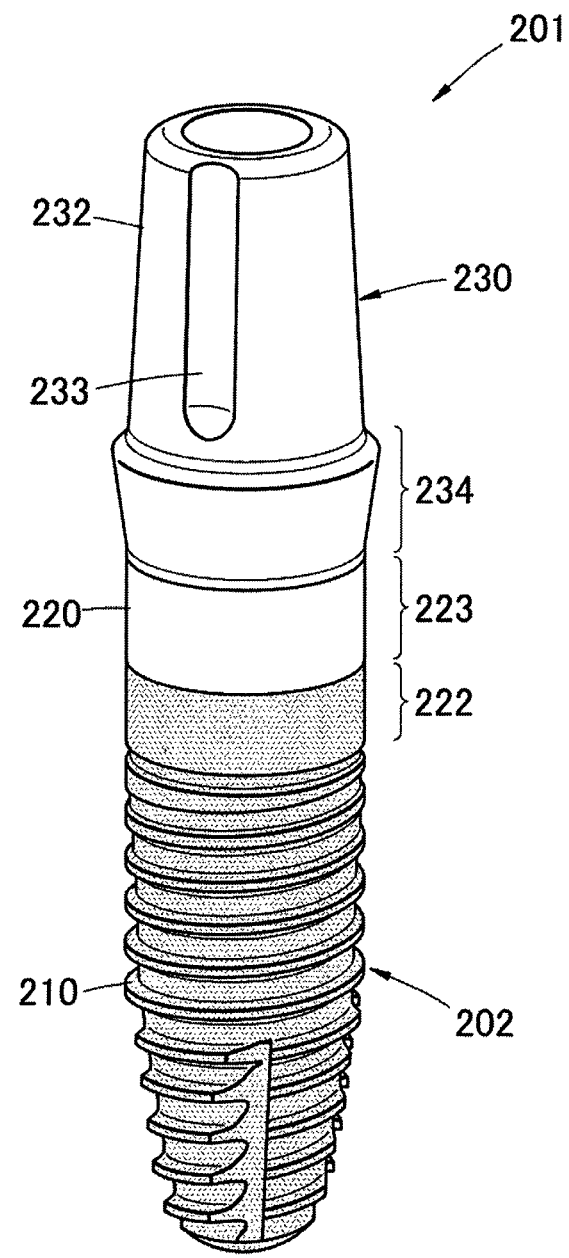
FIG. 6 a perspective view showing an artificial dental root according to one embodiment of the present invention.

FIG. 6 is a perspective view of an artificial dental root 1 according to one embodiment of the present invention. FIG. 7 is a sectional view of the artificial dental root 1 shown in FIG. 6, and FIG. 8 is an exploded view of the same.

Figure 8:
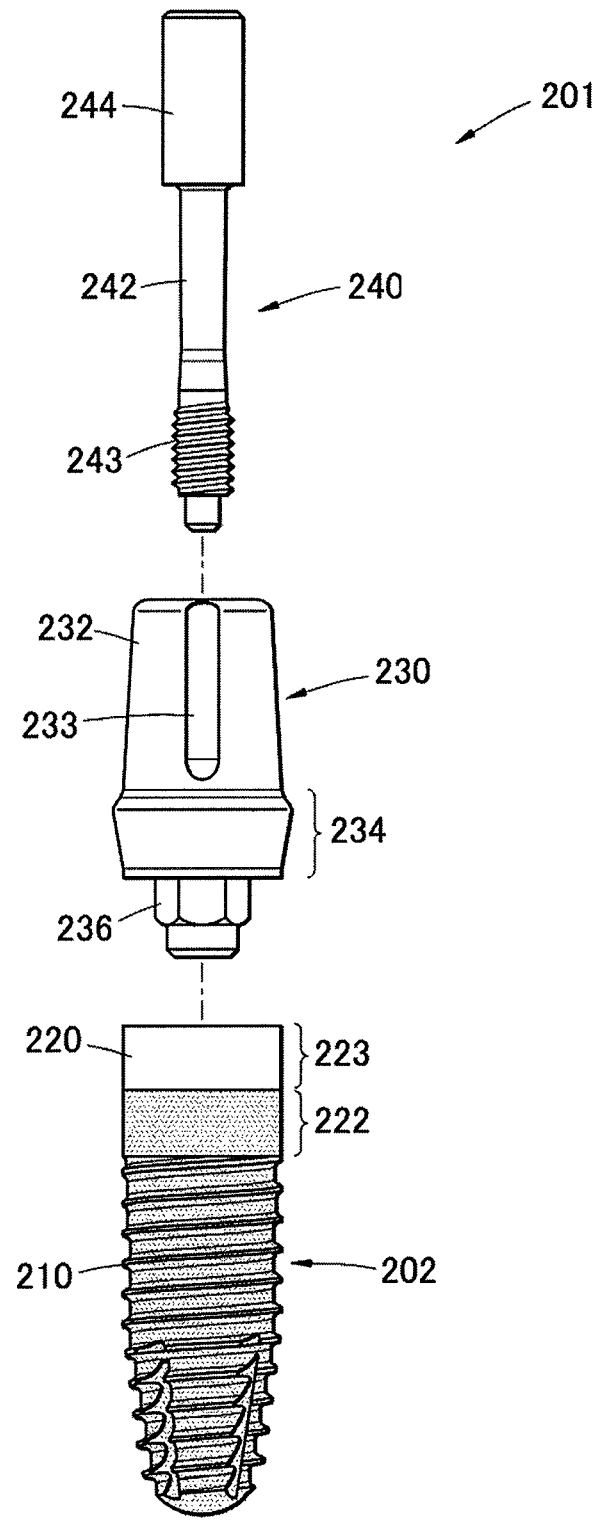
FIG. 8 is an exploded view of the artificial dental root shown in FIG. 6.

As shown in FIG. 8, an artificial dental root 201 consists of a fixture 202, an abutment 230 and an abutment screw 240, and this corresponds to the substrate 1.

It is possible to use, as the material of the artificial dental root 201, known materials, for example, metallic materials such as titanium, a Ti alloy, a Co—Cr alloy and a molybdenum alloy, and ceramic materials such as alumina ceramics.

The fixture 202 consists of two elements such as a base body 210 and an interdental papilla forming body 220. The external surface of the base body 210 and the interdental papilla forming body 220 forms a continuous contour and is coplanar with each other.

In the present second embodiment, a mirror polishing portion 223 and an abutment surface (inclined portion) 234 of the top portion of the dental implant body are coated with a biocompatible material such as MPC. As describe above, by coating with the biocompatible material, inhibition of bone resorption of the periphery of the implant as well as a deposition state of gingival epithelia and gingival connective tissues after secondary surgery can be improved. Since plaque deposition to the gingival penetration portion of the implant body is inhibited to a considerable degree, it is possible to further ensure long-term prognosis of the dental implant and to apply the implant even under compromised conditions where the implant could not be applied in the prior art. The coating method is the same as that according to the first embodiment, and also the biocompatible material and adhesive constituting the binder layer to be used are the same as those according to the first embodiment. Herein, the MPC polymer layer of the implant surface can be used as a carrier for controlled release of the drug.

The base body 210 has a slightly tapering generally cylindrical shape and an external thread 212 is formed on the outer peripheral surface. The ridge of the external thread 212 becomes higher towards the tip side. The ridge of the tip side is partially notched and has a function of preventing the bone component from the thread from turning after embedding by entering into the notch portion after embedding. The fixture 202 is firmly embedded inside the alveolar bone by the external thread 212.

A hollow bottomed hole 214 is formed in the base body 210 and an internal thread 217 is formed on the internal wall surface. This internal thread 217 is engaged with a thread 243 of an abutment screw 240 described hereinafter. At the end portion of the hollow bottomed hole 214 of the base body 210, a concave receiving portion 216 for receiving turnably a connection end 224 of the interdental papilla forming body 220. The end of the base body 210 constitutes a connection end portion 218 which is tight contact with the proximal end of the interdental papilla forming body 220.

The interdental papilla forming body 220 has a generally cylindrical shape, and includes a principal plane portion 221 at the distal side and includes a convex connection end 224 at the proximal side. The diameter of the connection end 224 having a cylindrical shape is less than that of the principal plane portion 221 having a cylindrical shape. The convex connection end 224 having a cylindrical shape is turnably inserted into the receiving portion 216 of the base body 210.

A through hole is formed in the interdental papilla forming body 220, and an internal thread 227 is formed on the internal wall surface. This internal thread 227 is used to transport and mount to the base body 210 embedded and inserted into the alveolar bone, together with a threaded cover cap having a role of a cap until the bone is repaired and adhered. At the distal side of the through hole of the interdental papilla forming body 220, a concave cavity portion having a regular hexagonal shape for receiving a fitting end 236 of an abutment 230 is provided.

In the principal plane portion 221 of the interdental papilla forming body 220, a mirror finished surface 223 curved convexly towards the proximal side of the alveolar bone is formed on at least on the side peripheral surface corresponding to the cheek side, and other portions are formed of a rough surface 222. That is, the site to be contacted with gingival is subjected to mirror finishing, while the site to be joined with osseous papilla is roughened by mechanical means and/or chemical means. Sandblasting is used as mechanical means for roughening, and coating of calcium phosphate is used to increase affinity with the bone. Since a rough surface 222 and a mirror finished surface 223 are formed on the side peripheral surface of the interdental papilla forming body 220 having a cylindrical shape, there is an advantage such as easy production.

The abutment 230 has a generally cylindrical shape, and includes an artificial tooth mounting portion 232 at the distal side, includes an inclined portion 234 at the intermediate portion, and includes a fitting end 236 at the proximal side. The external size of the fitting end 236 having a regular hexagonal shape is less than the diameter of the artificial tooth mounting portion 232 having a cylindrical shape and an inclined portion 234. The convex fitting end 236 having a regular hexagonal shape is fitted and inserted into a cavity portion of the interdental papilla forming body 220. As shown in FIG. 8, the artificial tooth mounting portion 232 has a locking groove 233 extending in the longitudinal direction and an artificial tooth is fitted and inserted into the artificial tooth mounting portion 232 along the locking groove 233.

Figure 7:
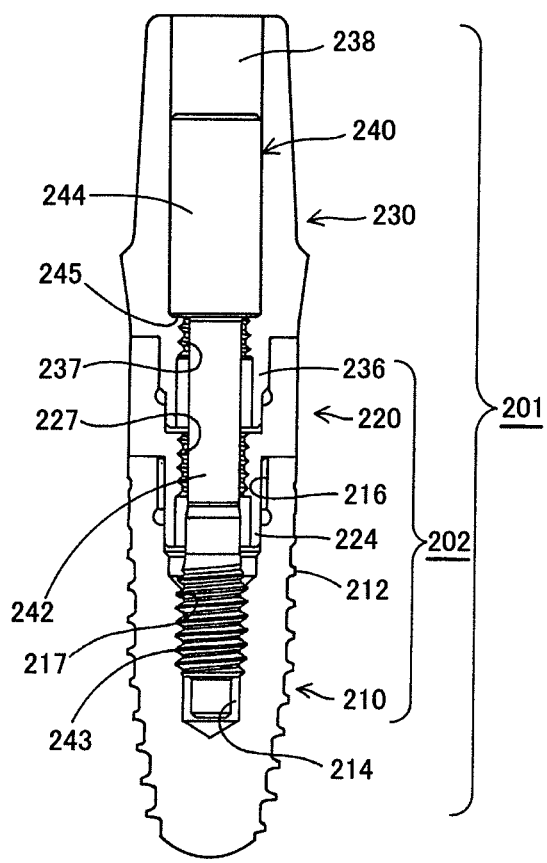
FIG. 7 is a sectional view of the artificial dental root shown in FIG. 6.

As shown in FIG. 7, a through hole with a two-stepped structure having a large diameter at the distal side and having a small diameter at the proximal side is formed in the abutment 230, and an internal thread 237 is formed on an internal wall surface of the proximal side of the through hole. This internal thread 237 is used to simultaneously transport and mount the abutment 230 and the abutment screw 240 into the interdental papilla forming body 220 of the fixture 2 embedded and fixed in the alveolar bone. The large diameter portion at the distal side is the size which enables insertion of the axis portion 242 of the abutment screw 240, while the small diameter portion at the proximal side is the size which enables insertion of the a thread 243 of the abutment screw 240. A topper portion 245 for receiving an axis portion 242 of the abutment screw 240 is formed at the intermediate portion of the through hole where the diameter portion changes to the small diameter portion at proximal side from the large diameter portion at distal side.

Therefore, the hollow bottomed hole 214 of the base body 210, the through hole of the interdental papilla forming body 220 and the through hole with a two-stepped structure of the abutment 230 are coaxially formed, and the abutment screw 240 is inserted in the hole in which these holes are communicated in a line.

As shown in FIG. 8, the abutment screw 240 has a generally columnar shape with a two-stepped structure having a large diameter at the distal side and having a small diameter at the proximal side. That is, the abutment screw 240 consists of an upset head portion 244 into which an insertion appliance (so-called driver) is mounted to the concave head portion thereof, and an axis portion 242 having a small diameter extending at the proximal side of the upset head portion 244. A thread 243 is formed at the distal portion of the axis portion 242. As described previously, this thread 243 is respectively engaged with the internal thread 217 of the base body 210 and the internal thread 237 of the abutment 230.

EXAMPLE 1

A cardiac blood pump according to the present invention was produced in the following manner. A Co—Cr—Mo alloy with the composition of Co-28Cr-6Mo was used as the material constituting a substrate. Silica was used as the material of a binder layer and MPC was used as a biocompatible material.
(1) First, a cardiac blood pump made of a Co—Cr—Mo alloy (composition: Co-28Cr-6Mo alloy) was formed by a conventional method and the resulting cardiac blood pump was subjected to ultrasonic cleaning in an acetone solution.
(2) Then, the cardiac blood pump was subjected to a high Cr treatment (nitric acid treatment) by dipping in a 20 to 40% nitric acid for 30 minutes.
(3) This cardiac blood pump subjected to the nitric acid treatment was placed in a plasma treatment apparatus and subjected to an oxygen plasma treatment for 5 minutes to form an oxide on a surface, and then high-density Cr—OH was formed.
(4) The treated cardiac blood pump was quickly dipped in an ethanol (95) solution of 5% by weight methacryloyloxypropyltrimethoxysilane, 0.1% by weight IRGACURE (D2959), 93.9% by weight ethanol (anhydrous) and 0.1% by weight succinic acid.
(5) Subsequently, the cardiac blood pump was heat-treated at 70° C. for 3 hours (normal pressure).
(6) Subsequently, the cardiac blood pump was dipped in an aqueous 0.25 to 1.00 mol/L MPC solution and then photo-irradiated with 350 nm ultraviolet rays at 60° C. for 23 minutes to 180 minutes to form an MPC polymer.
(7) After formation of the MPC polymer, the cardiac blood pump was washed by dipping in ethanol overnight.

According to the above steps, it was possible to produce a cardiac blood pump coated uniformly with MPC as a biocompatible material in a high concentration.

Figure 9:
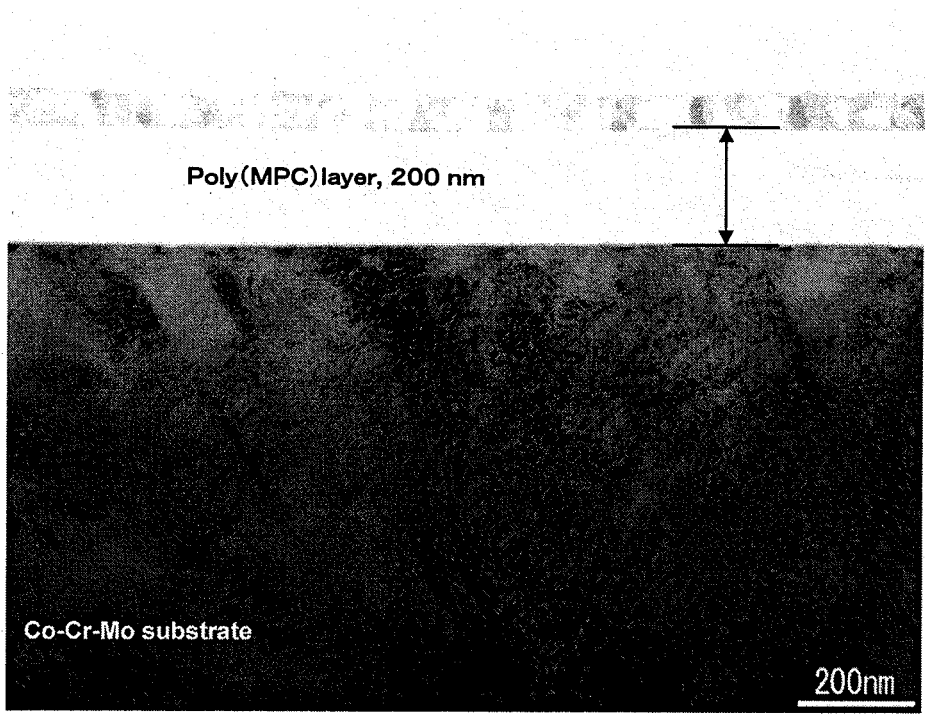
FIG. 9 is a TEM image of a cross section of the cardiac blood pump.

FIG. 9 is a TEM image of a cross section of the cardiac blood pump. As shown in FIG. 9, it was confirmed that a uniform biocompatible material layer is formed on the surface thereof.

(Measurement of Protein Adsorption Characteristics)

Figure 10:
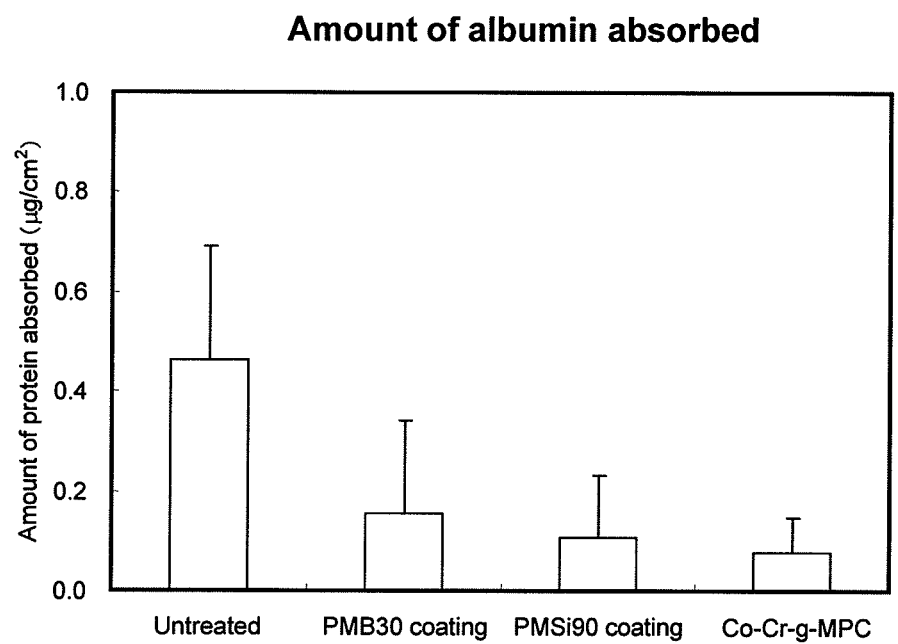
FIG. 10 is a graph showing adsorption properties of albumin to the cardiac blood pump of Example 1.
Figure 11:
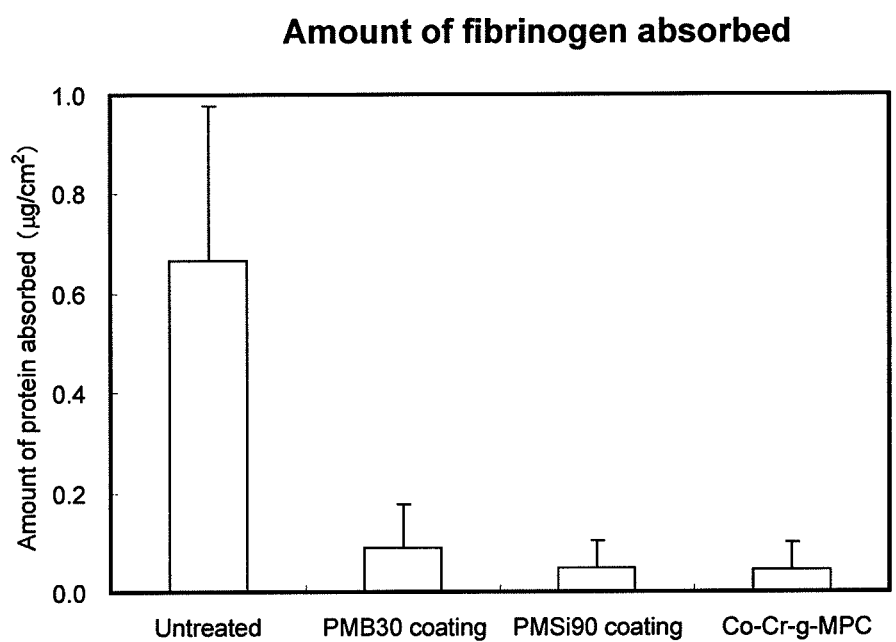
FIG. 11 is a graph showing adsorption properties of fibrinogen to the cardiac blood pump of Example 1

With respect to the respective samples shown below, the measurement of protein adsorption characteristics was carried out. The results are shown in FIG. 10 to FIG. 11. An untreated cobalt-chromium alloy, an MPC copolymer-treated cobalt-chromium alloy (PMB30), an MPC copolymer-treated cobalt-chromium alloy (PMB90) and an MPC graft-treated cobalt-chromium alloy (Co—Cr—Mo-g-MPC) were used as samples.

As a result, it was found that as the MPC content in the biocompatible material layer increases, the amount of albumin or fibrinogen adsorbed to the biocompatible material layer decreases, whereas, as the MPC content decreases, the amount of the protein adsorbed decreases.

Therefore, according to the present invention, the effect of stably exhibiting biocompatibility is exerted even when used in vivo, and therefore it becomes unnecessary to use a drug capable of inhibiting a biological defense reaction, thus making it possible to avoid the side effect due to the drug.

The biocompatible polymer layer on a surface can also be used as a drug eluting type medical device (particularly stent) and, even if the drug remains on the stent surface after elution, the polymer layer causes neither inflammatory reaction nor thrombus formation.

EXAMPLE 2

In the same manner as described above, a dental implant according to the present invention was produced and tested.

Similar to the above, it was found that as the MPC content in the biocompatible material layer increases, the amount of albumin or fibrinogen adsorbed to the biocompatible material layer decreases, whereas, as the MPC content decreases, the amount of the protein adsorbed decreases.

Therefore, it is possible to improve inhibition of bone resorption of the periphery of the implant as well as a deposition state of gingival epithelia and gingival connective tissues after secondary surgery by grafting the mirror polishing portion, the abutment surface, so-called healing cap surface of the top portion of the implant body with MPC.

Since plaque deposition to the gingival penetration portion of the implant body is inhibited to a considerable degree, it is possible to further ensure long-term prognosis of the dental implant and to apply the implant even under compromised conditions where the implant could not be applied in the prior art.

The invention claimed is:

1. A medical device comprising:
a substrate capable of forming hydroxyl groups,
a biocompatible material layer, and
a binder layer provided between the substrate and the biocompatible material layer formed through a dehydration-condensation reaction of at least one silicon alkoxide selected from the group consisting of methacryloyloxypropyltrimethoxysilane, methacryloyloxypropylmethyldimethoxysilane, methacryloyloxypropyltriethoxysilane, and acryloyloxypropyltrimethoxysilane,
wherein:
hydroxyl groups are formed on a surface of the substrate by a surface treatment,
the biocompatible material layer is formed from a polymer containing phosphorylcholine groups,
the substrate and the biocompatible material layer are joined via the binder layer,
the binder layer is covalently bonded with the hydroxyl groups and the biocompatible material,
only the binder layer contains a photopolymerization initiator, and
the substrate is formed from at least one member selected from the group consisting of titanium, cobalt-chromium alloy, cobalt-chromium-molybdenum alloy, nickel-chromium alloy, stainless steel, and titanium base alloy.

2. The medical device according to claim 1, wherein the biocompatible material layer is formed by covalent bonding of the polymer containing phosphorylcholine groups as a graft polymer chain.

3. A medical device comprising:
a substrate capable of forming hydroxyl groups;
a biocompatible material layer, and
a binder layer provided between the substrate and the biocompatible material layer formed through a dehydration-condensation reaction of at least one silicon alkoxide selected from the group consisting of methacryloyloxypropyltrimethoxysilane, methacryloyloxypropylmethyldimethoxysilane, methacryloyloxypropyltriethoxysilane, and acryloyloxypropyltrimethoxysilane, wherein:

hydroxyl groups are formed on a surface of the substrate by a surface treatment, the biocompatible material layer is formed from a polymer containing phosphorylcholine groups, and has a thickness from 10 to 200 nm, the substrate and the biocompatible material layer are joined via the binder layer covalently bonded with the hydroxyl groups and the biocompatible material, and only the binder layer contains a photopolymerization initiator.

4. The medical device according to claim 1, wherein the contact angle of the biocompatible material layer to water is 30° or less.

5. The medical device according to claim 1, wherein the concentration of phosphorus atoms measured by X-ray photoelectron spectroscopy of the biocompatible material layer is 4.6 atomic % or more.

6. The medical device according to claim 1, wherein the medical device is a blood pump for an artificial heart, a blood pump for an auxiliary artificial heart, an artificial valve, a stent or a pacemaker.

7. The medical device according to claim 1, wherein the medical device is a dental implant.

8. A method for producing a medical device having a biocompatible material layer laminated thereon, the method comprising:
   a) a step of surface-treating a substrate formed from a material containing a metal component capable of forming hydroxyl groups to form hydroxyl groups on a surface of the substrate,
   b) a step of forming a binder layer containing a photopolymerization initiator through a dehydration-condensation reaction of at least one silicon alkoxide selected from the group consisting of methacryloyloxypropyltrimethoxysilane, methacryloyloxypropylmethyldimethoxysilane, methacryloyloxypropyltriethoxysilane, and acryloyloxypropyltrimethoxysilane, on the substrate using the hydroxyl groups as a starting point, and
   c) a step of immersing the substrate in a solution containing a biocompatible material and irradiating the substrate with ultraviolet rays, thereby polymerizing the biocompatible material at least at a position to form a biocompatible material layer on the binder layer.

9. The method for producing a medical device according to claim 8, wherein the step a) further comprises a pretreatment process in which a surface of the substrate formed from at least one alloy selected from the group consisting of cobalt-chromium, cobalt-chromium-molybdenum, nickel-chromium, and stainless steel is subject to a nitric acid treatment to increase the chromium concentration on the substrate surface.

* * * * *